United States Patent
Sasaki et al.

(12)

(10) Patent No.: US 6,187,939 B1
(45) Date of Patent: Feb. 13, 2001

(54) METHOD FOR PREPARING FATTY ACID ESTERS AND FUEL COMPRISING FATTY ACID ESTERS

(75) Inventors: Toshio Sasaki, Ichihara; Tomoyuki Suzuki, Tsukuba; Fumio Okada, Niihama, all of (JP)

(73) Assignee: Sumitomo Chemical Company, Limited, Osaka (JP)

( * ) Notice: Under 35 U.S.C. 154(b), the term of this patent shall be extended for 0 days.

(21) Appl. No.: 09/392,478

(22) Filed: Sep. 9, 1999

(30) Foreign Application Priority Data

Sep. 9, 1998 (JP) .................................. 10-255285
Feb. 8, 1999 (JP) .................................. 11-029940

(51) Int. Cl.$^7$ .................................. C11C 1/00; C11C 3/04
(52) U.S. Cl. ..................... 554/169; 554/174; 435/134; 435/135
(58) Field of Search ............................ 554/169; 435/134, 435/135; 508/463

(56) References Cited

U.S. PATENT DOCUMENTS

| 2,418,898 | 4/1947 | Murphy et al. ......................... 554/30 |
| 2,521,742 | 9/1950 | Paterson et al. ...................... 554/167 |
| 5,455,370 | 10/1995 | Demmering et al. ................. 554/169 |
| 5,468,887 | * 11/1995 | Gupta .................................... 554/169 |
| 5,532,392 | * 7/1996 | Gheorghiu ............................ 554/169 |
| 5,713,965 | 2/1998 | Foglia et al. ............................ 44/388 |
| 5,773,636 | 6/1998 | Demmering et al. ................. 554/169 |
| 5,908,946 | 6/1999 | Stern et al. ............................ 554/167 |

FOREIGN PATENT DOCUMENTS

| 0593524B1 | 4/1994 | (EP) . |
| 57-47396 | 3/1982 | (JP) . |
| 7-197047 | 8/1995 | (JP) . |
| 9-235573 | 9/1997 | (JP) . |
| WO 98/12169A1 | 3/1998 | (WO) . |

OTHER PUBLICATIONS

Jackson, M.A., et al.; *Journal of the American Oil Chemists 'Society*, US, American Oil Chemists 'Society, Champaign, IL, Mar. 1996, vol. 73, No. 3; pp. 353–356.
Table 2, Physikalische Daten primater, linearer, ungesattigler Fettalkohole, pp. 430–445 (no translation).
K.S. Markley, Fatty Acids Part 2, p. 798 (1961).
Partial English translation of "Oleochemical Products Guide Book", pp. 799–800.
Kreutzer, *JAOCS*, vol. 61, No. 2 (Feb. 1984).

* cited by examiner

*Primary Examiner*—Ellen M. McAvoy
(74) *Attorney, Agent, or Firm*—Birch, Stewart, Kolasch & Birch LLP

(57) ABSTRACT

Fatty acid esters, which are prepared by reacting fats and oils with an alcohol in the absence of a catalyst under a condition under which at least one of the fats and oils and the alcohol is in a supercritical state, are useful as fuels such as diesel fuels, lubrication base oils or fuel additives.

9 Claims, No Drawings

METHOD FOR PREPARING FATTY ACID ESTERS AND FUEL COMPRISING FATTY ACID ESTERS

BACKGROUND OF THE INVENTION

1. Field of the Invention

The present invention relates to a method for preparing fatty acid esters by the reaction of fats and oils with alcohols, and a fuel comprising fatty acid esters which are prepared by such a method.

2. Prior Art

Fats and oils comprise triglycerides, that is, esters of glycerol with fatty acids, and fatty acid esters which are obtained by the transesterification of fats and oils with alcohols are widely used as industrial raw materials or medicines.

A method is reported, which produces diesel fuels or lubrication base oils containing fatty acid esters as substitutes for mineral oils by the transesterification of fats and oils with alcohols. For example, the methods disclosed in JP-A-7-197047 and JP-A-9-235573 prepare a diesel fuel by reacting waste edible oils and methanol in the presence of sodium hydroxide.

U.S. Pat. No. 5,713,965 discloses a method for the preparation of a diesel fuel and a lubricant containing fatty acid esters by the reaction of fats and oils with alcohols in hexane as a solvent in the presence of lipase.

Furthermore, a method is known, which prepares fatty acid esters by the reaction of fats and oils with alcohols while introducing a catalyst under pressure (Ullmanns Enzyklopädie der technischen Chemie, 4th Ed, Vol. 11 (1976) 432). That is, fats and oils are reacted with the 7 to 8 times excessive amount of alcohols at a temperature of 240° C. under a pressure of 10 MPa in the presence of an alkali catalyst or a zinc catalyst.

However, the methods for the preparation of fatty acid esters using catalysts have some drawbacks such that the yield of fatty acid esters decreases due to the by-production of fatty acid salts, fatty acids, etc., or the process steps become complicated to remove catalysts, fatty acid salts, etc. Thus, it is highly desired to provide a simple method for the preparation of fatty acid esters at a high yield.

Hitherto, waste fats and oils are drained with no treatment, treated with coagulating agents and then discarded, burnt, or buried in ground. However, such post-treatment of waste fats and oils become the focus of public attention as one cause of environmental pollution, since the waste fats and oils are poorly decomposed under environmental conditions. Thus, a method for the preparation of a useful material containing fatty acid esters such as a diesel fuel from waste fats and oils in the absence of a catalyst is very advantageous from the viewpoint of environmental pollution, and the recover and recycle of resources.

SUMMARY OF THE INVENTION

One object of the present invention is to provide a simple method for the preparation of fatty acid esters at a high yield from fats and oils and alcohols.

Another object of the present invention is to provide a fuel such as a diesel fuel, a lubrication base oil or a fuel additive, comprising fatty acid esters which can be prepared by a simple method.

Accordingly, the present invention provides a method for preparing a fatty acid ester comprising the step of reacting fats and oils with an alcohol in the absence of a catalyst under a condition under which at least one of the fats and oils and the alcohol is in a supercritical state.

Furthermore, the present invention provides a fuel, a diesel fuel, a lubrication base oil or a fuel additive, comprising at least one fatty acid ester which is prepared by the above method of the present invention.

DETAILED DESCRIPTION OF THE INVENTION

The main reaction in the method according to the present invention is represented by the following reaction scheme:

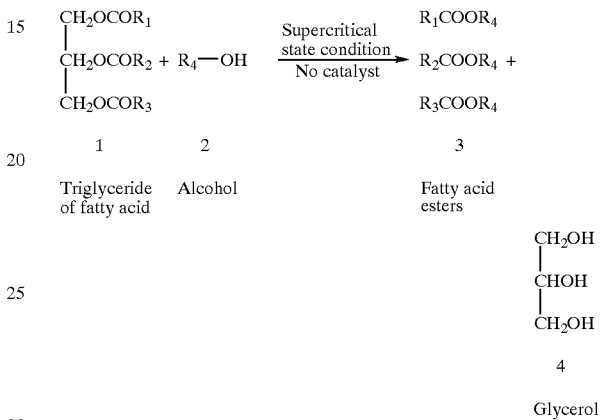

wherein $R_1$, $R_2$ and $R_3$ represent independently each other an aliphatic hydrocarbyl group having 6 to 24 carbon atoms and 0 to 5 double bonds, and $R_4$ is a a hydrocarbyl group having 1 to 10carbon atoms, or a hydrocarbyloxyl group-substituted hydrocarbyl group having 2 to 10 carbon atom in total.

Fats and oils used in the method of the present invention comprise a triglyceride 1 in the above reaction scheme, and may be natural or synthetic ones.

Specific examples of fats and oils include lard oil, chicken oil, butter oil, beef tallow, cocoa butter oil, corn oil, peanut oil, cottonseed oil, soybean oil, palm oil, olive oil, safflower oil, linseed oil, coconut oil, oak oil, almond oil, apricot kernel oil, beef bone fat, walnut oil, castor oil, chaulmoogra oil, chinese vegetable tallow, cod-liver oil, cotton seed stearin, sesame oil, deer oil, dolphin oil, sardine oil, mackerel oil, horse fat, seam (lard), bone oil, sheep oil, neat's foot oil, palm oil, palm kernel oil, harbor porpoise oil, shark oil, sperm whale oil, tung oil, whale oil, etc. Furthermore, mixtures of two or more fats and oils, fats and oils containing diglyceride and/or monoglyceride, partially modified (e.g. oxidized or reduced) fats and oil, and the like may also be used.

Fats and oils may contain other materials. Examples of the other materials include crude oil, heavy oil, gas oil, mineral oil, essential oil, coal, fatty acids, saccharides, metal powders, metal salts, proteins, amino acids, hydrocarbons, cholesterol, flavors, coloring compounds, enzymes, perfumes, alcohols,. fibers, resins, rubbers, paints, cements, detergents, aromatic compounds, aliphatic compounds, smut, glass, sand, nitrogen-containing compounds, sulfur-containing compounds, phosphorus-containing compounds, halogen-containing compounds, etc.

It is preferable to remove such other materials by a suitable method such as filtration, distillation, and the like prior to the reaction, when the other materials may participate in the reaction, for example, they interfere with the reaction, or when they are solid materials and cause the blocking of facilities used in the production process.

Distillation methods include vacuum distillation, steam distillation, molecular distillation, extractive distillation, etc.

Fats and oils may be waste fats and oils, waste edible oils, and the like.

The kind of an alcohol (compound 2 in the above reaction scheme) is not limited. Preferably, an alcohol of the formula (1):

R—OH    (1)

wherein R is a hydrocarbyl group having 1 to 10 carbon atoms, or a hydrocarbyloxyl group-substituted hydrocarbyl group having 2 to 10 carbon atom in total is used.

Examples of a hydrocarbyl group having 1 to 10 carbon atoms include alkyl groups, aralkyl groups, alkenyl groups, alkynyl groups, etc.

Specific examples of alcohols of the formula (1) in which R is an alkyl group are methanol, ethanol, n-propanol, isopropanol, n-butanol, isobutanol, tert.-butanol, pentanol, hexanol, cyclohexanol, heptanol, etc.

Specific examples of alcohols of the formula (1) in which R is an aralkyl group are benzyl alcohol, α-phenethyl alcohol, β-phenethyl alcohol, etc. Among them, benzyl alcohol is preferable.

Specific examples of alcohols of the formula (1) in which R is an alkenyl group are allyl alcohol, 1-methylallyl alcohol, 2-methylallyl alcohol, 3-buten-1-ol, 3-biten-2-ol, etc. Among them, allyl alcohol is preferable.

Specific examples of alcohols of the formula (1) in which R is an alkynyl group are 2-propyn-1-ol, 2-butyn-1-ol, 3-butyn-1-ol, 3-butyn-2-ol, etc.

Specific examples of alcohols of the formula (1) in which R is a hydrocarbyloxy group-substituted hydrocarbyl group having 2 to 10 carbon atom in total are 2-methoxyethanol, 2-methoxypropanyl, 3-methoxybutanol, etc.

In particular, an alcohol of the formula (1) in which R is an alkyl group having 1 to 4 carbon atom is preferable. Specific examples of such an alcohol include methanol (R=a methyl group), ethanol (R=an ethyl group), propanol (R=a propyl group), isopropanol (R=an isopropyl group), n-butanol (R=a n-butyl group), isobutanol (R=an isobutyl group) and tert.-butanol (R=a tert.-butyl group). Among them, methanol and ethanol are preferable, and methanol is more preferable.

Alcohols may be used singly or in admixture of two or more alcohols.

Optical isomers of an alcohol may be used, when the alcohol has optical isomers.

Typical examples of fatty acid esters 3 produced by the above reaction scheme include esters of valeric acid, caproic acid, enanthoic acid, caprylic acid, pelargonic acid, capric acid, undecylic acid, lauric acid, tridecylic acid, myristic acid, pentadecylic acid, palmitic acid, heptadecylic acid, stearic acid, nonadecanoic acid, arachidic acid, behenic acid, lignoceric acid, cerotic acid, heptacosanoic acid, montanic acid, melissic acid, lacceric acid, crotonic acid, isocrotonic acid, undecylenic acid, oleic acid, elaidic acid, cetoleic acid, erucic acid, brassidic acid, sorbic acid, linoleic acid, linolenic acid, arachidonic acid, propiolic acid, stearolic acid, nervonic acid, licinoleic acid, (+)-hydnocarpic acid, (+)-chaulmoogric acid, etc. The kind of an alcohol residue in an ester depends on the kind of an alcohol used. For example, when methanol is used as an alcohol, a methyl ester is obtained. When ethanol is used as an alcohol, an ethyl ester is obtained.

When fatty acid residues have optical isomers, fatty acid esters 3 include the fatty acid esters of such optical isomers.

According to the method of the present invention, glycerol 4 is obtained in addition to fatty acid esters.

Reaction conditions employed in the method of the present invention will be explained.

The method of the present invention is characterized in that a fat and an oil is reacted with an alcohol in the absence of a catalyst under conditions where the fat and oil and/or the alcohol is in a supercritical state.

A supercritical state herein used is now explained.

A material has specific three states, that is, a gas state, a liquid state and a solid state. Furthermore, a material has a fluid state in which it is not condensed by the application of a pressure, when a temperature exceeds a supercritical temperature. Such a state of a material is a supercritical state.

A fluid in a supercritical state has different properties from those of a liquid or a gas. In a supercritical state, the density of a fluid is close to that of a liquid, the viscosity of a fluid is close to that of a gas, and the thermal conductivity and diffusion coefficient of a fluid are intermediate between those of a gas and a liquid. Thus, a fluid functions as a non-liquid solvent, and is favorable to mass transfer due to its low viscosity and high diffusivity. In addition, such a liquid can achieve high heat transmission due to its high heat conductivity. The reactivity in a supercritical state is higher than that in usual gas and liquid states since a supercritical state is a very special state as explained above, and thus a transesterification reaction is much facilitated.

Herein, "a condition under which at least one of the fat and oil and the alcohol is in a supercritical state" means one of the following conditions (a), (b) and (c):

(a) a temperature condition under which the mixture of a fat and an oil, and an alcohol is in a supercritical state;

(b) a temperature condition under which an alcohol is in a supercritical state;

(c) a temperature condition under which a fat and an oil is in a supercritical state.

Among the above conditions, condition (a) or (b) is preferable.

Condition (b) will be explained more in detail.

When methanol is used as an alcohol, a reaction is carried out at a temperature of at least 240° C., since the critical temperature of methanol is 240° C. When ethanol is used as an alcohol, a reaction is carried out at a temperature of at least 243° C., since the critical temperature of ethanol is 243° C. When propanol is used as an alcohol, a reaction is carried out at a temperature of at least 264° C., since the critical temperature of propanol is 264° C. When isopropanol is used as an alcohol, a reaction is carried out at a temperature of at least 236° C., since the critical temperature of isopropanol is 236° C. When butanol is used as an alcohol, a reaction is carried out at a temperature of at least 287° C., since the critical temperature of butanol is 287° C. When isobutanol is used as an alcohol, a reaction is carried out at a temperature of at least 275° C., since the critical temperature of isobutanol is 275° C. When tert.-butanol is used as an alcohol, a reaction is carried out at a temperature of at least 233° C., since the critical temperature of tert.-butanol is 233° C.

The upper limit of a reaction temperature is not limited. Preferably, a reaction temperature does not exceed 400° C.

The upper limit of a reaction pressure is not limited. A pressure does not exceed 25.0 MPa, since the improvement of the pressure resistance of a reaction vessel will cost much. The lower limit of a reaction pressure is not critical, and is preferably 0.4 MPa or higher to increase a yield.

Another characteristic of the present invention is that no or few catalyst is used. That is, a catalyst is not added to a reaction system, or a catalyst is added to a reaction system in a very small amount, for example, 0.1 wt. % or less of the weight of fats and oils. The substantial nonuse of a catalyst provides some advantages such that a series of industrial process steps are simplified, and production costs can be reduced. In addition, by-products such as fatty acid salts or free fatty acids are not formed, and thus fatty acid esters can be prepared at a high yield.

Herein, catalysts mean conventional alkali catalysts, zinc catalysts, and the like. Examples of alkali catalysts include sodium hydroxide, potassium hydroxide, sodium alkoxides, potassium alkoxides, alakaline earth metal alkoxides, alkali metal carbonates, alkaline earth metal carbonates, alkali metal titanates, alkaline earth metal titanates, etc.

A reaction time in the method of the present invention depends on various factors such as the kinds of fats and oils and alcohols, other reaction conditions, a required yield, etc. In general, a reaction time is from 1 to 480 minutes. When a reaction time is less than one minute, the reaction may not sufficiently proceed. A reaction time longer than 480 minutes may be unfavorable from the viewpoint of a production cost.

The molar amount of an alcohol per one mole of triglycerides of fatty acids (compound 1 in the above reaction scheme), which are contained in fats and oils, depends on the kinds of fats and oils and alcohols. In general, an alcohol is preferably used in an amount of 3 to 1,000 moles per one mole of triglyceride.

The reaction of the present invention may be carried out in various reaction modes. For example, the reaction can be carried out in a batch system or a continuous system.

In the method of the present invention, fats and oils and alcohols may be homogeneously mixed, or they may be separated to form two phases insofar as they can be reacted each other.

When fats and oils and alcohols are separated to form two phases, the reaction can proceed effectively by the increase of a contact area of two phases by stirring.

A reaction mixture after the completion of the reaction contains fatty acid esters, glycerol, and unreacted excessive alcohols. A reaction mixture may contain unreacted raw materials, and other impurities.

Fatty acid esters and glycerol are isolated from a reaction mixture and purified to a desired purity for respective applications.

A purification method is not limited, and any conventional purification method such as distillation, extraction, and the like may be employed according to the properties of produced fatty acid esters.

For example, unreacted alcohols are evaporated and recovered from a reaction mixture by vacuum distillation, etc., and then the resulting mixture after the evaporation of alcohols is separated into a light liquid comprising fatty acid esters and a heavy liquid comprising glycerol. Furthermore, a reaction mixture is separated into a light liquid comprising fatty acid esters and a heavy liquid comprising glycerol, and then unreacted alcohols are evaporated off from both liquids.

Apart from distillation such as vacuum distillation, unreacted alcohols may be separated from a reaction mixture by mixer-settler extraction, liquid-liquid extraction, extraction with a pulse column, jet type extraction, Podbielniak rotating extraction, etc. Alcohols can be completely separated to recover only fatty acid esters, while fatty acid esters containing residual alcohols may be recovered.

In general, a fatty acid ester product prepared by the method of the present invention is a mixture comprising at least two fatty acid esters, when natural fats and oils are used. In such a case, a mixture may be used without isolation, or a specific fatty acid ester or esters may be isolated by any conventional method such as distillation, extraction, etc., if necessary.

Fatty acid esters prepared by the method of the present invention can be used alone or in admixture with other component or components in accordance with requirements for specific applications, for example, a fuel such as a diesel fuel, a lubrication base oil and a fuel additive.

In the case of using as a diesel fuel, ignition properties and a viscosity of a fuel are important, as described in NEW EDITION "AUTOMOBILE TECHNOLOGY HANDBOOK" (edited by SHADAN-HOJIN JIDOSHA GIJUTUKAI). If fatty acid esters having a relatively low viscosity are used, they will cause the abrasion or seizing of a diesel engine. Thus, it is necessary to use fatty acid esters having a suitable viscosity for a diesel engine. If fatty acid esters have very large molecular weights, they will cause bad odors or smokes. Such fatty acid esters are not desirable.

For example, the methyl esters, ethyl esters, isopropyL esters and isobutyl esters of fatty acids are preferably used as diesel fuels. Among them, isopropyl esters and isobutyl esters of fatty acids are high performance diesel fuels even at low temperatures.

The viscosity of fatty acid esters is also important when they are used as lubrication base oils. Fatty acid esters having a relatively high viscosity are desired so that they exhibit high lubrication properties when they are used in hot seasons, while those having a relatively low viscosity and high flowability are preferred when they are used in cold seasons or cold areas. Thus, a wide variety of fatty acid esters can be used as lubrication base oils.

Fuel additives are added to fuels mainly for the purpose of decreasing friction, and have substantially the same functions as lubricant oils. Thus, fuel additives are required to have the same properties as lubrication base oils.

Fatty acid esters prepared by the method of the present invention may contain glycerol, unreacted excessive alcohols, unreacted fats and oils, and other impurities, which may be contained in the reaction mixture after the completion of the reaction, insofar as they do not cause any problems when the fatty acid esters are used for certain applications.

The conversion of fats and oils can be increased depending on the application of fatty acid esters by repeating the above reaction under the conditions according to the present invention.

The present invention provides a simple method for the preparation of fatty acid esters at a high yield from fats and oils and alcohols, and a fuel such as a diesel fuel, a lubrication base oil or a fuel additive, comprising fatty acid esters which are prepared by such a simple method. When the method of the present invention is applied to waste fats and oils, useful fuels and the like can be easily prepared from the waste fats and oils Thus, the present invention is very useful from the viewpoint of the reuse of resources and the prevention of environmental pollution.

The present invention will be illustrated by the following examples, which will not limit the scope of the present invention in any way.

The amounts of reactant materials and products were calculated by an area percentage method based on the total amounts of the ions of materials which were detected using a gas chromatography-mass spectrum analyzer (manufactured by YOKOGAWA ELECTRIC CORPORATION). The conversion of fats and oils was calculated from the weights of fats and oils before and after the reaction by sampling fats and oils which remained in a reaction mixture after the reaction.

In Examples and Comparative Examples, waste soybean oil, which is one example of waste edible oils, was used, except that fresh soybean oil was used in Example 9.

EXAMPLE 1

Waste soybean oil (4.317 g) and methanol (1.713 g) were charged into an autoclave (made of SUS 316; length: 15 cm; inner diameter: 0.8cm; capacity: 9 ml), and placed in an oven with laying the autoclave on its side. Then, the temperature of the oven was raised to 300° C. to initiate a reaction, and the reaction was carried out without stirring. After 30 minutes from the initiation of the reaction, the autoclave was quenched. When the autoclave was cooled to room temperature, the reaction mixture was recovered from the autoclave. The products were analyzed by the above-described method. The major products were methyl esters of fatty acids, and the conversion of waste soybean oil was 100 wt. %.

The autoclave used in this Example was not equipped with a pressure gauge. Thus, the following experiment was done to estimate a pressure in the autoclave in the course of the reaction:

A pressure gauge was attached to the same autoclave as used in this Example. Then, the same amounts of waste soybean oil and methanol were charged into the autoclave and heated with a sand bath to the same temperature as that employed in this Example, and a pressure was measured.

An estimated pressure in the course of the reaction was 6.5 MPa.

The results are shown in Table 1.

EXAMPLES 2–3 and COMPARATIVE EXAMPLE 1

Waste soybean oil and methanol were reacted in the same manner as in Example 1 except that a reaction temperature was changed as shown in Table 1. The results are shown in Table 1.

It can be seen from those results that the conversion at 220° C. was much lower than that at 240° C. or higher.

EXAMPLE 4

Waste soybean oil (5.509 g) and methanol (1.016 g) were charged into an autoclave (made of SUS 316; capacity: 9 ml) and heated to 300° C. with a sand bath to initiate a reaction. After 30 minutes from the initiation of the reaction, the autoclave was quenched. When the autoclave was cooled to room temperature, the reaction mixture was recovered from the autoclave. The products were analyzed by the above-described method. The major products were methyl esters of fatty acids, and the conversion of waste soybean oil was 95 wt. %.

An estimated pressure, which was measured in the same way as that in Example 1, was 0.4 MPa. The results are shown in Table 1.

EXAMPLES 5–6 and COMPARATIVE EXAMPLE 2

Waste soybean oil and methanol were reacted in the same manner as in Example 4 except that a reaction temperature was changed as shown in Table 1. The results are shown in Table 1.

It can be seen from those results that the conversion at 220° C. was much lower than th at at 240° C. or higher.

EXAMPLES 7–8

Waste soybean oil and methanol were reacted in the same manner as in Example 1 except that a reaction temperature and a reaction time were changed as shown in Table 1. The results are shown in Table 1.

The reaction proceeded at a conversion of 100% under the conditions of Example 8, although the reaction time was as short as 10 minutes.

EXAMPLE 9

Fresh soybean oil (available from WAKO JUNYAKU Co., Ltd.) and methanol were reacted under the same reaction conditions as those in Ex amp le 1. The results are shown in Table 1.

It can be seen from those results that the reaction proceeded at a high conversion when fresh soybean oil was used in place of waste soybean oil.

TABLE 1

|  | Temp. (° C.) | Pressure (MPa) | Time (min.) | Molar ratio of methanol to glyceride | Conversion of soybean oil (wt. %) | Amount of soybean oil (g) | Amount of Methanol (g) |
|---|---|---|---|---|---|---|---|
| Ex. 1 | 300 | (6.5) | 30 | 10 | 100 | 4.317 | 1.713 |
| Ex. 2 | 270 | — | 30 | 10 | 75 | 4.324 | 1.743 |
| Ex. 3 | 250 | — | 30 | 10 | 29 | 4.313 | 1.712 |
| C. Ex. 1 | 220 | — | 30 | 10 | 10 | 4.301 | 1.793 |
| Ex. 4 | 300 | (0.4) | 30 | 5 | 95 | 5.509 | 1.016 |
| Ex. 5 | 270 | — | 30 | 5 | 32 | 5.524 | 1.069 |
| Ex. 6 | 250 | — | 30 | 5 | 29 | 5.496 | 1.035 |
| C. Ex. 2 | 220 | — | 30 | 5 | 4 | 5.45 | 1.05 |
| Ex. 7 | 300 | (7.5) | 30 | 20 | 100 | 3.636 | 2.525 |
| Ex. 8 | 350 | (14) | 10 | 5 | 100 | 5.218 | 1.096 |
| Ex. 9 | 300 | — | 30 | 10 | 100 | 4.362 | 1.759 |

In Examples 1–9 and Comparative Examples 1–2, the autoclave was laid on its side in an oven or a sand bath to carry out a reaction with maintaining a large contact area between a soybean oil and methanol.

EXAMPLE 10

Waste soybean oil (0.396 g) and methanol (5.734 g) were charged into an autoclave equipped with a pressure gauge (manufactured by NITTO KOATSU KABUSHIKIKAI-SHA; made of SUS 316; length: 10 cm; inner diameter: 1.5 cm; capacity: 20 ml), and an air in the autoclave was replaced with argon gas. Then the autoclave was heated to 300° C. with a sand bath to initiate a reaction. Apressure in the course of a reaction was 10MPa. After 30 minutes from the initiation of the reaction, the autoclave was quenched. When the autoclave was cooled to room temperature, the reaction mixture was recovered from the autoclave. The products were analyzed by the above-described method. The conversion of waste soybean oil was 100 wt. %, and 0.463 g of the methyl esters of fatty acids were obtained. The results are shown in Table 2.

EXAMPLE 11

Waste soybean oil (0.367 g) and methanol (3.737 g) were charged into an autoclave equipped with a pressure gauge (made of SUS 316; length: 15 cm; inner diameter: 0.8 cm; capacity: 9 ml), and an air in the autoclave was replaced with argon gas. Then the autoclave was heated to 250° C. with a sand bath to initiate a reaction. A pressure in the course of a reaction was 10 MPa. After 1 (one) hour from the initiation of the reaction, the autoclave was quenched. When the autoclave was cooled to room temperature, the reaction mixture was recovered from the autoclave. The products were analyzed by the above-described method. The conversion of waste soybean oil was 100 wt. %, and 0.394 g of the methyl esters of fatty acids were obtained. The results are shown in Table 2.

EXAMPLE 12

Waste soybean oil (0.305 g) and methanol (3.759 g) were charged into an autoclave equipped with a pressure gauge (made of SUS 316; capacity: 9 ml), and an air in the autoclave was replaced with argon gas. Then the autoclave was heated to 240° C. with a sand bath to initiate a reaction. A pressure in the course of a reaction was 10 MPa. After 30 minutes from the initiation of the reaction, the autoclave was quenched. When the autoclave was cooled to room temperature, the reaction mixture was recovered from the autoclave. The products were analyzed by the above-described method. The conversion of waste soybean oil was 74 wt. %, and 0.124 g of the methyl esters of fatty acids were obtained. The results are shown in Table 2.

COMPARATIVE EXAMPLE 3

Waste soybean oil (0.325 g) and methanol (3.738 g) were charged into an autoclave equipped with a pressure gauge (made of SUS 316; capacity: 9 ml), and an air in the autoclave was replaced with argon gas. Then the autoclave was heated to 180° C. with a sand bath to initiate a reaction. A pressure in the course of a reaction was 4 MPa. After 1 (one) hour from the initiation of the reaction, the autoclave was quenched. When the autoclave was cooled to room temperature, the reaction mixture was recovered from the autoclave. The products were analyzed by the above-described method. The conversion of waste soybean oil was 30 wt. %. The results are shown in Table 2.

EXAMPLE 13

Waste soybean oil (2.117 g) and methanol (5.991 g) were charged into an autoclave equipped with a pressure gauge (manufactured by NITTO KOATSU KABUSHIKIKAISHA; made of SUS 316; length: 10 cm; inner diameter: 1.5 cm; capacity: 20 ml), and an air in the autoclave was replaced with argon gas. Then the autoclave was heated to 300° C. with a sand bath to initiate a reaction. A pressure in the course of a reaction was 9 MPa. After 30 minutes from the initiation of the reaction, the autoclave was quenched. When the autoclave was cooled to room temperature, the reaction mixture was recovered from the autoclave. The products were analyzed by the above-described method. The conversion of waste soybean oil was 60 wt. %, and 0.572 g of the methyl esters of fatty acids were obtained. The results are shown in Table 2.

COMPARATIVE EXAMPLE 4

Waste soybean oil (0.350 g) and methanol (1.508 g) were charged into an autoclave equipped with a pressure gauge (made of SUS 316; capacity: 9 ml), and an air in the autoclave was replaced with argon gas. Then the autoclave was heated to 200° C. with a sand bath to initiate a reaction. A pressure in the course of a reaction was 2.5 MPa. After 60 minutes from the initiation of the reaction, the autoclave was quenched. When the autoclave was cooled to room temperature, the reaction mixture was recovered from the autoclave. The products were analyzed by the above-described method. The conversion of waste soybean oil was 35 wt. %. The results are shown in Table 2.

COMPARATIVE EXAMPLE 5

Waste soybean oil (0.095 g) and a largely excessive amount of sodium methylate were reacted in methyl acetate as a solvent at 80° C. for 8 hours. The conversion of waste soybean oil was 100 wt. %, and 0.033 g of methyl esters of fatty acids were obtained. In addition to the methyl ester of fatty acids, 0.017 g of fatty acids were formed.

TABLE 2

| | Temp. (° C.) | Pressure (MPa) | Time (min.) | Molar ratio of methanol to glyceride | Conversion of soybean oil (wt. %) | Amount of soybean oil (g) | Amount of Methanol (g) |
|---|---|---|---|---|---|---|---|
| Ex. 10 | 300 | 10 | 30 | 400 | 100 | 0.396 | 5.734 |
| Ex. 11 | 250 | ↑ | 60 | 300 | 100 | 0.367 | 3.737 |
| Ex. 12 | 240 | ↑ | 30 | 300 | 74 | 0.305 | 3.759 |
| C. Ex. 3 | 180 | 4 | 60 | 300 | 30 | 0.325 | 3.738 |
| Ex. 13 | 300 | 9 | 30 | 75 | 60 | 2.117 | 5.991 |
| C. Ex. 4 | 200 | 2.5 | 60 | 120 | 35 | 0.35 | 1.508 |

The reactions in Examples 10–13 and Comparative Examples 3 and 4 were carried out with placing the autoclaves in the sand bath with their bottom downward. Thus, a contact area between the waste soybean oil and methanol decreased, and therefore the reactivity was lower than that achieved by the reaction carried out with laying the autoclave on its side.

What is claimed is:

1. A method for preparing a fatty acid ester consisting essentially of the step of reacting fats and oils with an alcohol in the absence of a catalyst under a condition under which at least one of the fats and oils and the alcohol is in a supercritical state.

2. A method according to claim 1, wherein the reaction is carried out under a condition under which said alcohol is in a supercritical state.

3. A method according to claim 1, wherein a reaction pressure is not exceeding 25 MPa.

4. A method according to claim 1, wherein said alcohol is an alcohol of the formula:

R—OH wherein R is a hydrocarbyl group having 1 to 10 carbon atoms, or a hydrocarbyloxyl group-substituted hydrocarbyl group having 2 to 10 carbon atom in total.

5. A method according to claim 4, wherein the R group in the formula: R—OH is an alkyl group having 1 to 4 carbon atoms.

6. A method according to claim 5, wherein the R group in the formula: R—OH is a methyl group or an ethyl group.

7. A method according to claim 6, wherein the R group in the formula: R—OH is a methyl group.

8. A method according to claim 1, wherein said fat and oil is a waste fat and oil.

9. A method according to claim 1, wherein said fat and oil is a waste edible oil.

\* \* \* \* \*